(12) United States Patent
Shire et al.

(10) Patent No.: US 6,324,429 B1
(45) Date of Patent: Nov. 27, 2001

(54) CHRONICALLY IMPLANTABLE RETINAL PROSTHESIS

(75) Inventors: Doug Shire, Ithaca, NY (US); Joseph Rizzo, Boston; John Wyatt, Sudbury, both of MA (US)

(73) Assignees: Massachusetts Eye and Ear Infirmary, Boston; Massachusetts Institute of Technology, Cambridge, both of MA (US)

( * ) Notice: Subject to any disclaimer, the term of this patent is extended or adjusted under 35 U.S.C. 154(b) by 0 days.

(21) Appl. No.: 09/306,964

(22) Filed: May 7, 1999

Related U.S. Application Data
(60) Provisional application No. 60/084,745, filed on May 8, 1998.

(51) Int. Cl.[7] ....................................... A61N 1/08
(52) U.S. Cl. ............................................. 607/54; 623/6.63
(58) Field of Search ................................. 607/53, 54, 116; 623/6.63

(56) References Cited

U.S. PATENT DOCUMENTS

| | | |
|---|---|---|
| 4,373,218 | 2/1983 | Schachar . |
| 4,601,545 | 7/1986 | Kern . |
| 4,628,933 | * 12/1986 | Michelson . |
| 4,704,123 | 11/1987 | Smith . |
| 4,759,762 | 7/1988 | Grendahl . |
| 4,816,031 | 3/1989 | Pfoff . |
| 4,842,601 | 6/1989 | Smith . |
| 5,016,633 | * 5/1991 | Chow . |
| 5,024,223 | * 6/1991 | Chow . |
| 5,108,429 | 4/1992 | Wiley . |
| 5,109,844 | * 5/1992 | De Juan, Jr. et al. . |
| 5,171,266 | 12/1992 | Wiley et al. . |
| 5,250,167 | 10/1993 | Adolf et al. . |
| 5,334,629 | 8/1994 | Zirino . |
| 5,411,540 | 5/1995 | Edell et al. . |

(List continued on next page.)

FOREIGN PATENT DOCUMENTS

| | | |
|---|---|---|
| WO89/06520 | 7/1989 | (WO) . |
| WO 92/03989 | 3/1992 | (WO) . |
| WO94/23334 | 10/1994 | (WO) . |
| WO 97/06751 | 2/1997 | (WO) . |

OTHER PUBLICATIONS

Kern, Seymour P. "Bifocal, electrically switched intraocular and eyeglass molecular lenses", SPIE vol. 601, *Ophthalmic Optics* (1985).

*Primary Examiner*—Mark Bockelman
(74) *Attorney, Agent, or Firm*—Choate, Hall & Stewart

(57) ABSTRACT

A combination of silicon processing technology advances and increased understanding of the mechanisms underlying phosphene generation in human retinas by surface electrical stimulation has now made it possible to conceive of a chronically implantable retinal prosthesis for the blind which will restore some useful vision to patients over at least several degrees of their former field of view. These thin, strong, and flexible epiretinal devices are constructed of or encapsulated in known biocompatible materials which will have a long working life in the eye's saline environment. The function of the implants is to electrically stimulate the ganglion cell layer at the surface of the retina using controlled current sources. Due to the exceptionally low mass of the implant and its flexible, nearly planar form, patient discomfort and fluid drag caused by the implant minimized. These physical atttributes also substantially reduce the potential of harm to the most delicate structure of the eye, the retina, and therefore enhance the long term safety and biocompatibility of the device. Since no micro-cables are required to be attached to the device, and its overall form and edges are rounded, the device is not expected to stress the retina during chronic implantation. A provision is also made for nutrients to reach the retinal cells underneath the device to assure their long-term health.

17 Claims, 2 Drawing Sheets

U.S. PATENT DOCUMENTS

| | | |
|---|---|---|
| 5,443,506 | 8/1995 | Garabet . |
| 5,476,494 | 12/1995 | Edell et al. . |
| 5,556,423 * | 9/1996 | Chow et al. . |
| 5,575,813 | 11/1996 | Edell et al. . |
| 5,597,381 * | 1/1997 | Rizzo, III . |
| 5,800,530 | 9/1998 | Rizzo, III . |
| 5,865,839 * | 2/1999 | Doorish . |
| 5,873,901 * | 2/1999 | Wu et al. . |
| 5,895,415 * | 4/1999 | Chow et al. . |
| 5,935,155 * | 8/1999 | Humayun et al. . |
| 5,944,747 * | 8/1999 | Greenberg et al. . |
| 6,032,062 * | 2/2000 | Nisch . |
| 6,230,057 * | 5/2001 | Chow et al. . |

* cited by examiner

CHRONICALLY IMPLANTABLE RETINAL PROSTHESIS

This application claims the priority of U.S. Provisional Patent Application No. 60/084,745, filed May 8, 1998, incorporated herein by reference

FIELD OF THE INVENTION

The present invention relates generally to visual prostheses, and more specifically, the invention relates to retinal implants which employ controlled electrical current pulses to create the impression of the presence of light in patients whose photoreceptor cells (rods and cones) are not functioning by stimulating the ganglion cells at the retina surface.

BACKGROUND OF THE INVENTION

Some important and common forms of blindness result from degeneration of the rods and cones of the eye and in these cases the sole output cells (i.e., ganglion cells) are relatively spared. The development of a fully functioning intraocular prosthesis integrated into a single unit has been a long time goal.

In the human eye, the ganglion cell layer of the retina becomes a monolayer at a distance of 2.5–2.75 mm from the foveola center. Since the cells are no longer stacked in this outer region, this is the preferred location for stimulation with an epiretinal electrode array. The feasibility of a visual prosthesis operating on such a principle has been demonstrated by Humayun et al. in an experiment in which the retinas of patients with retinitis pigmentosa, age-related macular degeneration, or similar degenerative diseases of the eye were stimulated using bundles of insulated platinum wire. The patients were under local anesthesia, and they described seeing points of light which correctly corresponded with the region of the retina in which the stimulus was applied (Humayun, M., et al., *Archiv. Ophthalmol.*, 114: 40–46, 1996). The form of the stimulating device was, however, not suited for chronic implantation. The threshold for perception was reported to be in the range of 0.16–70 mC/cm$^2$. This confirmed the results of earlier experiments on animal subjects by the instant inventors and others which indicated that strong evoked cortical potentials could be observed when rabbit retinas were stimulated using passive microfabricated electrode arrays similar in some respects to the ones proposed in the current invention (Rizzo, J. F., et al., ARVO Poster Session Abstract, *Investigative Ophthalmology and Visual Science*, 37: S707, 1996; Walter, P., et al. *Investigative Ophthalmology and Visual Science*, 39: S990, 1998). The instant inventors have, with others, performed three surgical procedures using microfabricated electrode arrays and similar in technique to those described by Humayun and confirmed that a consistent response to input electrical stimuli could be noted by the patient.

The task of creating a retinal implant has been addressed by Chow, in U.S. Pat. No. 5,016,633, who proposed a subretinal implant based on a microphotodiode array. The procedure involved in its implantation is so biologically intrusive, however, that successful implementation of such a device in human subjects has not been reported. Furthermore, an entirely passive array will be rather insensitive under normal lighting conditions, and an array powered from outside the body by means of a direct electrical connection will likely lead to infections and again, be so intrusive as to be objectionable.

Earlier designs of the present inventors placed all components of the prosthesis on the retinal surface (U.S. patent application Ser. No. 19/074,196, filed May 7, 1998, and U.S. Pat. No. 5,800,530, both of which are incorporated herein by reference). It became quickly apparent that the delicate retina could not withstand the mechanical burden which was at least partially the result of the relatively thick profile of the microelectronic components. A later prototype included one significant change in design—the bulky microelectronic components were moved anteriorly within the eye, off of the retinal surface. In this configuration, the microelectronics are held in a custom-designed intraocular lens, and only a thin ribbon containing the microelectrodes extends rearwardly to the retinal surface.

In summary, the present invention is a contribution to an ongoing area of development of visual prostheses which embodies the state of the art in both silicon processing technology and our understanding of the mechanisms underlying phosphene generation in human retinas by surface electrical stimulation. The feasibility of creating a chronically implantable retinal prosthesis capable of restoring some useful vision to blind patients over at least several degrees of their former field of view has been demonstrated.

SUMMARY OF THE INVENTION

The current invention is an improvement of prior art by some of the instant inventors in which a flexible, cantilevered epiretinal implant structure was first disclosed (U.S. Pat. Nos. 5,411,540 and 5,476,494, both of which are incorporated herein by reference). The primary improvement in the current invention is the monolithic integration of the signal processing, power conversion, control functions, and stimulating current sources on an ultrathin silicon membrane which is part of the implant itself and not physically removed from the retinal area to be stimulated. By making the electronics as flexible as the remainder of the implant, the biocompatibility of the overall device is greatly improved. Furthermore, the absence of micro-cables in a hybrid assembly makes the surgical procedure considerably simpler. While a polyimide-based extension of the essential silicon structure is not ruled out, it can be limited to a region extending not more than several mm beyond the silicon region's periphery.

The biocompatibility of the materials which are proposed to be employed in the fabrication of a chronically implantable device has been addressed by others, and in the current invention we propose a hermetic seal on the silicon-based portion of the device made possible by plasma enhanced deposition of amorphous silicon carbide (S. Bayliss, et al. *Thin Solid Films*, 297, 308–310, 1997; R. Hauert, et al. *Thin Solid Films*, 308–309, 191–194, 1997; R. Richardson, et al. *Biomaterials*, 14: 627–635, 1993). While it is of course essential for the implant to have a benign effect on the surrounding tissue in terms of cytotoxicity, cell adhesion and the absence of toxic electrochemical reactions at the electrode-electrolyte interface, it is also important that metal ions be kept away from the sensitive MOS circuitry. The multiple layer coating structure proposed in the current invention serves both these needs.

One object of the invention is to process and retransmit to the ganglion cells on the retina surface images which cover at least several degrees of a blind patient's former field of view. Since the precise mechanism by which the perception of light is elicited by electrical current injection to these cells is not fully understood, the circuitry used to perform the signal processing functions is envisioned to operate primarily in a slave mode, with control functions for the raster presentation of incoming video data performed externally where possible. The power dissipation of the implanted silicon circuit must be minimized to limit the requirements on the external power supply. In a preferred embodiment, the external circuitry could be mounted on a pair of eyeglasses or in the patient's pocket.

Another object of the invention is to provide an implantable device suitable for chronic use. That is, its components should be biocompatible; its mass and profile should be minimized; it should be epiretinal in placement; it should have a long working life in the eye environment; it should be highly flexible; and surgically tractable; and it should allow for the continued health of tissue which it covers.

These objects, together with other objects, features, and advantages of the invention will become more readily apparent from the following detailed description when taken in conjunction with the accompanying drawings.

BRIEF DESCRIPTION OF THE DRAWING

The invention is described with reference to the several figures of the drawing, in which.

DETAILED DESCRIPTION

Figure 1:
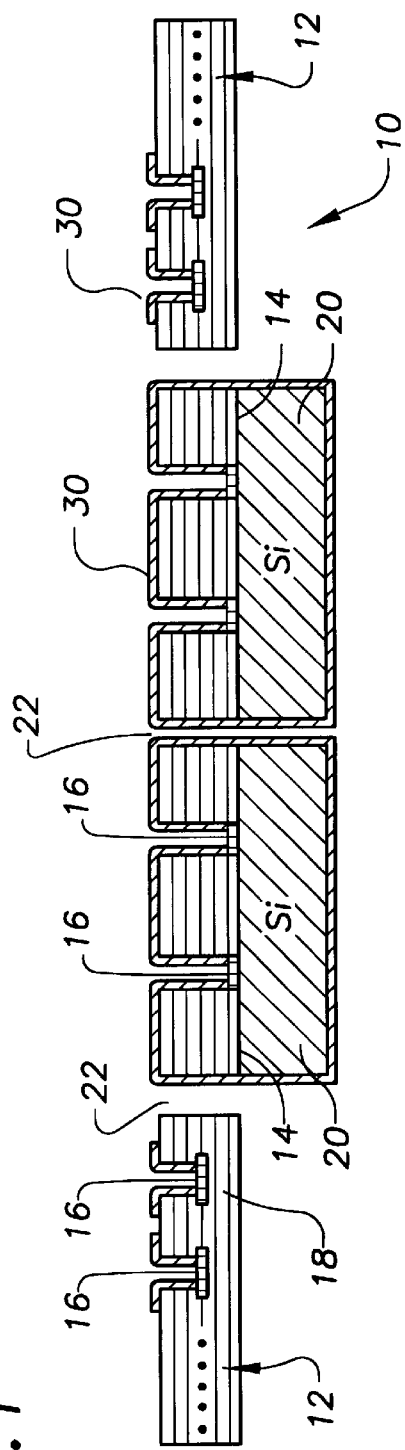
FIG. 1 is a cross-sectional view of a retinal implant according to the present invention.

The invention disclosed herein describes a new retinal implant whose components are disposed at the retinal surface. The design is made possible by advances in microfabrication technology, which is used to integrate highly complex electronic circuitry into exceptionally thin membranes that will rest on the retina without imparting excessive mechanical forces thereon. Favorable mechanical as well as optical interactions of the prosthesis with the retina are required if the prosthesis is to be clinically useful.

Modern microfabrication techniques are used to create the integrated, ultrathin, implantable complete retinal prosthesis which will contain a power receptacle, transistors and other active circuitry and microelectrodes, possibly constructed in a monolithic fashion. The device of the invention is ultrathin (roughly 5–15 $\mu$m in thickness) to minimize mechanical damage to the retina that can occur when a thicker or less flexible structure is placed in contact with the delicate and curved retina. The device may be fabricated with silicon or another semiconductor.

The device of the invention is "complete" in that it will: 1) be capable of receiving incoming signals that will transmit both power and signal; 2) contain active electronic circuitry to distribute charge to specific electrodes in relation to the incoming visual signal; and 3) contain metal electrodes through which currents can be delivered to the retina. Transmission of power and signal may be accomplished using either a laser or radiofrequency communication. For the former, the internal wireless power receptacle will be a photodiode array. For radiofrequency transmission, the internal power receptacle will be a pickup coil made of microfabricated wires of copper or some other conducting material. In the case of photonic communication, the prosthesis has a through and through three dimensional architecture such that a photodiode array would be situated on the side of the prosthesis facing the incoming light while the stimulating electrodes would be on the opposite side facing the retina.

The retinal prosthesis of the invention is embodied on a silicon or other semiconductor "membrane" which can flex to match the inner curvature of the retina. Flexibility will further limit the potential mechanical damage that might occur if the membrane were relatively inflexible and had to bend to match the curvature of the retina. The result of downward force generated by bending could damage the retina. A photodiode array, if included in the design, would have to be of a certain minimum thickness, otherwise the structure would be transparent to incoming light which would severely compromise power generation. As such, a photodiode array might be thicker than the rest of the device and may therefore protrude slightly from the surface.

We anticipate that the entire thickness of the device, even with a slightly thicker photodiode segment, would still be quite thin. Thinness is important to minimize the cross-sectional area of the device, minimizing elastic modulus. This reduces the downward force exerted on the retina by the device. This force can impact on the prosthesis and generate deleterious shear forces on the retina. One substantial advantage of this fully integrated "complete" microfabricated prosthesis is that a very complex electronic device can be built that will minimize potential damage because of its thinness and small cross-sectional area, so as to minimize downward force when the device is bent to match retinal curvature. Unacceptably large forces, greater than 10 mm Hg, can permanently damage retinal tissue, as described in our commonly owned patent U.S. Pat. No. 5,575,813, incorporated herein by reference.

The retinal prosthesis of the invention is electrically intricate enough to serve as a power receptacle and source with the capability of directing fixed currents for specified intervals to specific electrodes and mechanically small enough to be in contact with the retina without inducing mechanical damage.

The present invention includes a retinal implant device comprising a silicon substrate; CMOS circuitry fabricated on the silicon substrate, which performs signal processing, power management, control, and current stimulation functions; an electrode array, fabricated partially on the thinned silicon and partially on an attached polyimide layer; and means for receiving the power and data which are transmitted into the eye from an external transmitter, either through an inductor or a photodiode array; and passivating films (e.g. of amorphous silicon carbide) which enhance the device's biocompatibility. The silicon substrate is preferably a silicon-on-insulator type substrate. In another embodiment, the silicon may be replaced by another semiconductor substrate suitable for wafer thinning. In a preferred embodiment, the polyimide comprises PIQ-L100, manufactured by HD Microsystems, Inc., Wilmington, Del.

The present invention includes a design for a retinal implant for the purpose of restoring some useful vision to certain blind patients. The implant will be implanted through a small incision in the cornea. For the invention to work properly, the patient must have healthy optic nerves; consequently, the prime candidates for implants based on the current invention are persons with degenerative diseases such as retinitis pigmentosa or age-related macular degeneration. A cross sectional view of a prototype implant 10 appears in FIG. 1. At the outer extremes of the implant 10, an optional inductive coil 12 is shown. This coil 12 receives incoming power and data signals from a transmitter (not shown) which is external to the eye. An alternative method of receiving these signals is to use a photodiode array (not shown) which would be fabricated together with CMOS driver circuitry 14, shown in FIG. 3. In the latter case, the illumination would impinge on the bottom side of the implant, which faces the vitreous region of the eye in the preferred configuration.

Also shown in FIG. 1 are stimulating electrodes 16 which have been deposited on polyimide 18 and Si 20 surfaces. These electrodes 16 are made from an adhesion layer, e.g. titanium or chromium, a conducting layer such as gold, and a surface layer of iridium or titanium nitride, which is activated using a process of cyclic voltammetry to maximize the charge delivery capacity. Other materials with a high charge delivery capacity are also suitable for the electrode 16. The electrical connections between the individual stimulating electrodes 16 and the CMOS current driving circuitry 14 are not shown for clarity, and two levels of interconnects will be required to make all the necessary connections. The electrodes 16 disposed on the polyimide surface may be connected to the silicon layer 20 via an extension of the polyimide layer 18 and conductive traces contained therein. The silicon-based circuitry contains n-and p-type wells which extend throughout the thin membrane, and the entire silicon device is passivated with a multiple-layer dielectric stack 30 comprising stress-compensated silicon dioxide or silicon nitride and a surface layer consisting of plasma-deposited amorphous silicon carbide. The latter material has been shown to be biocompatible and to be extremely resistant to harsh chemical environments. The thickness of the silicon membrane used is in the range of 5–10 $\mu$m, and the polyimide layer 18 may be from 2–20 $\mu$m thick. The precise thicknesses to be used are limited at one extreme by the mechanical flexibility of the device, which must be able to flex without exerting unacceptably high forces on the retina, and, at the other, its ability to withstand handling during surgical implantation. The polyimide layer 18 may have surface treatments applied (e.g., ion bombardment). Such treatments further enhance the biocompatibility of the implant by modifying the microstructure of the surface so as to improve cell adhesion or surface hydrophilicity. In addition, the prosthesis surface may also contain chemicals such as growth factors or anti-inflammatory or anti-angiogenic factors to help tailor the local retinal response to the prosthesis. The diameter of the silicon region may be in the range of 2–3 mm, and the overall implant may range in diameter from 3–9 mm or be larger still. The implant may take any shape, including a disk or polygon. It may include extended protrusions or may comprise a plurality of interconnected nodes. Several via holes 22 are shown which allow nutrients to reach the retinal cells situated underneath the implant 10, assuring their continued health. The number of these via holes 22 are adjusted according to the overall diameter of the device, owing to the increased surface area of the larger diameter implants. Numerous smaller holes may also be substituted for the small number of large via holes shown in FIG. 3.

Figure 2:
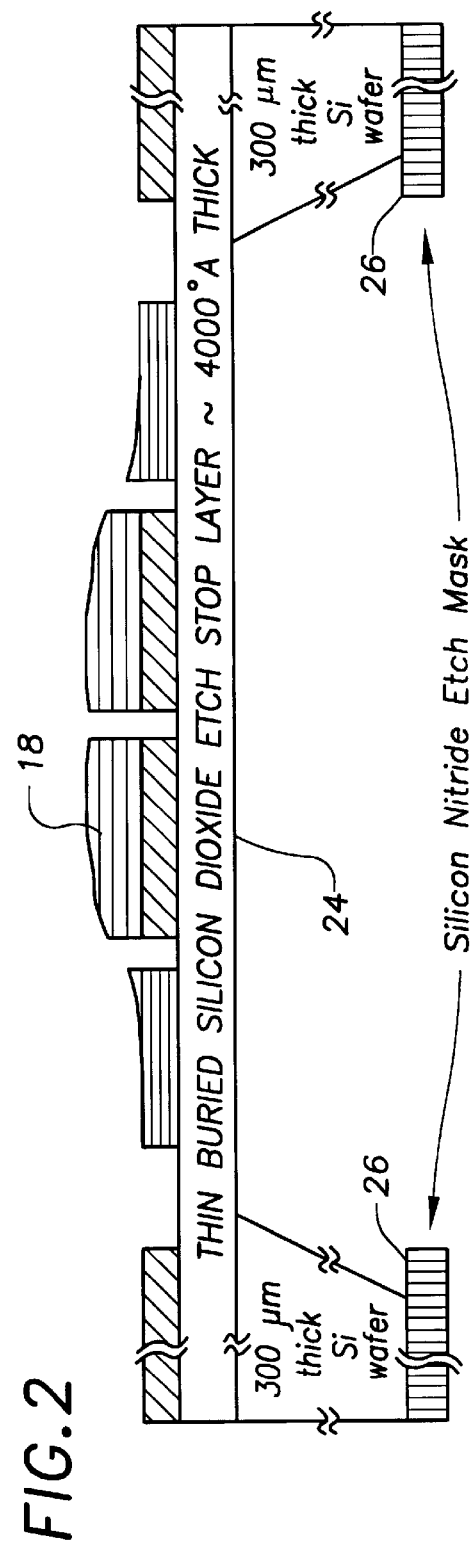
FIG. 2 is a cross-sectional view of a retinal implant according to the present invention when the fabrication process has been substantially completed.

In FIG. 2, a cross-sectional view of a device according to the present invention is shown in which the fabrication process is substantially complete. This diagram is intended to show an exemplary fabrication method for the thin silicon membrane containing the active CMOS circuitry utilizing silicon-on-insulator starting material. This method is also suited for mass production of devices according to the invention. Initially, the thin silicon epitaxial layer 20 above a silicon dioxide etch stop layer 24 is intact, and the wafer is processed according to a conventional CMOS method to create the desired power conditioning, control and data processing, and current driving or stimulating functions. Next, the wafer is thinned from the back side using a silicon nitride etch mask 26 and a tetramethyl ammonium hydroxide (TMAH) etchant. The thick (~300 $\mu$m) portion of the silicon wafer now acts as a mechanical support for the implant circuit which is suspended from all sides. The epitaxial silicon regions outside the active circuitry are then etched away using deep reactive ion etching, following which the polyimide layers are spun on and cured, and the interconnect and electrode metallizations are deposited. The edges of the device will be quite sharp, given their extreme thinness; thus, a final step in the fabrication process may involve rounding the outer polyimide edges of the prosthesis, e.g. by high pressure oxygen plasma etching.

Figure 3:
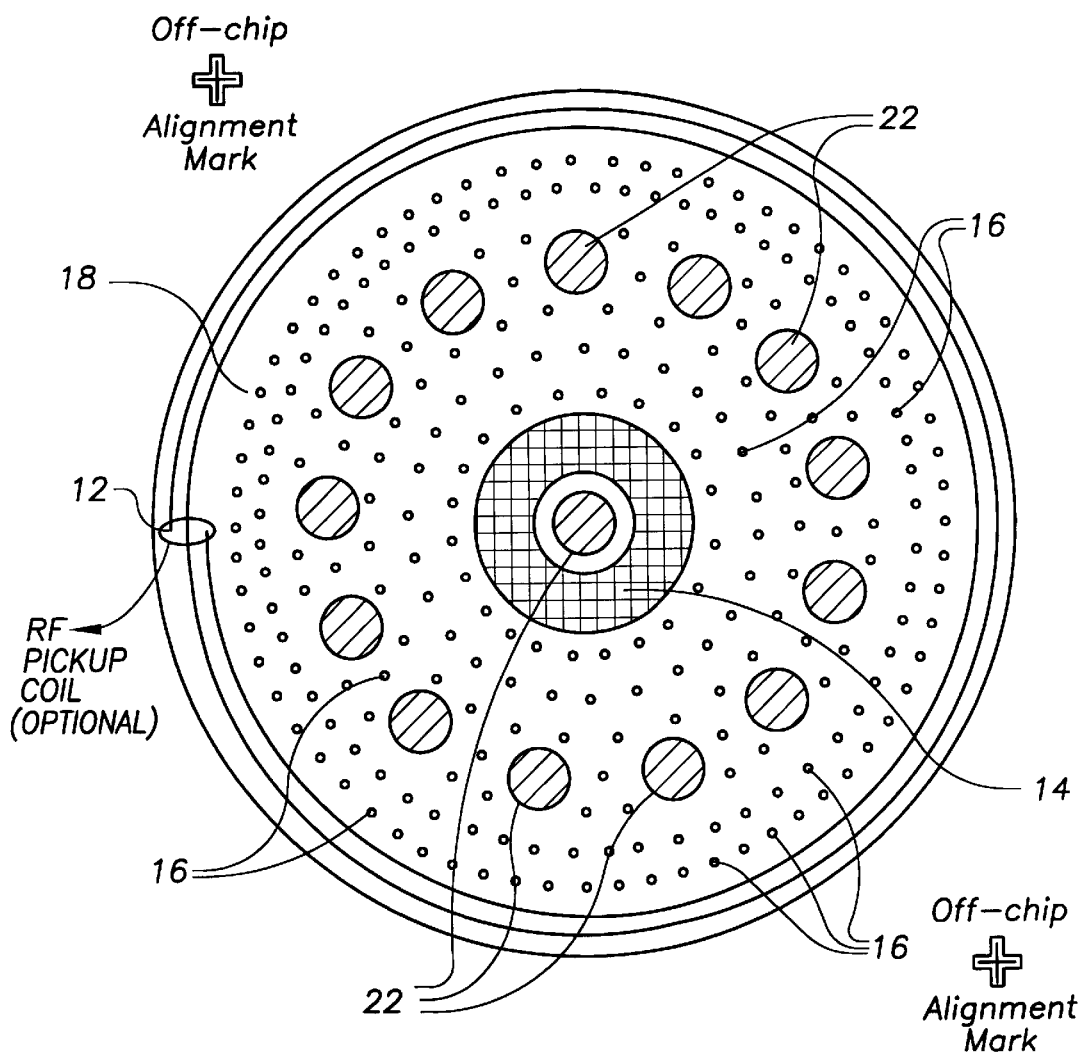
FIG. 3 is a plan-view sketch of the a retinal implant according to present invention.

In FIG. 3, a plan view sketch of the present invention is shown. Beginning at the outside edge of the polyimide 18, the optional RF coil 12 is shown without its connections to the silicon driver circuitry 14 for clarity. An array of microelectrodes 16 is shown which have an exposed surface layer of activated iridium or titanium nitride. A ring of via holes 22 is also shown together with another such hole in the center of the device. The CMOS silicon driver circuitry (not shown to scale) is shown in the center of the diagram. The functions performed by this circuitry are reception of power, control, and data signals from a source outside the eye, and direction of a programmable amount of DC electric current at programmable intervals to specific stimulating electrodes in the array. Again, the exact number and placement of the via holes 22 and stimulating microelectrodes 16 may be changed according to the desired overall size of the implant and according to the results of future acute human surgical trials using passive and/or active implant circuits. Furthermore, aside from the function of these micropores in allowing electrolytes and other nutrients to pass to and from the retinal surface to maintain normal homeostasis, the pores may also be useful by providing a site of attachment for cortical vitreous fibers of reactive processes of glial or other cells that might be induced to grow by the presence of a foreign body in the eye. Pores of an appropriate diameter are used to encourage penetration by extending cellular processes, thus increasing adhesive contact to the retina.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. An apparatus in contact with the inner surface of the retina, comprising:
   means to physically and conformally contact the retina surface with a flexible, strong multilayered, substantially planar structure, comprising:
      a thin semiconductor layer containing CMOS circuitry;
      a thin insulating layer disposed over at least a portion of the surface of the apparatus;
      stimulating electrodes disposed on the surface of the apparatus;
      stress-compensated passivation layers disposed about at least a portion of the apparatus, which enhance the apparatus' biocompatibility;
      means to receive power and data for said circuitry from outside the patient's body via electromagnetic radiation; and
      means to transmit said power and data signals
   wherein the apparatus electrically stimulates at least a portion of the surface of the retina.

2. The apparatus of claim 1, wherein
   said multilayered structure is monolithically integrated; and said multilayered structure is suited to mass production using common microfabrication equipment.

3. The apparatus of claim 1, wherein said thin semiconductor layer is the surface active layer of a silicon-on-insulator structure.

4. The apparatus of claim 3, wherein said stress-compensated passivation layers comprise a material from the group consisting of silicon oxide and nitride, and further comprise a surface layer of plasma-deposited amorphous silicon carbide.

5. The apparatus of claim 1, wherein said stimulating electrodes comprise iridium which has been activated and oxidized by cyclic voltammetry.

6. The apparatus of claim 1, wherein said stimulating electrodes comprise of titanium nitride which has been activated and oxidized by cyclic voltammetry.

7. The apparatus of claim 1, wherein said insulating layer comprises a polyimide.

8. The apparatus, of claim 7, wherein the polyimide comprises PIQ-L100 as provided by HD Microsystems, Inc.

9. The apparatus of claim 7, wherein the surface of said polyimide layer is modified by ion bombardment to enhance the biocompatibility of the material.

10. The apparatus of claim 7, wherein said polyimide layer is modified at its surface using chemicals from the group consisting of growth factors, anti-inflammatory factors, and anti-angiogenic factors.

11. The apparatus of claim 1, wherein said electromagnetic radiation has a wavelength between 400 and 700 nm and wherein said means to receive power and data comprises a photodiode array monolithically integrated with the remainder of the CMOS circuitry, and wherein said means of transmitting power is a laser.

12. The apparatus of claim 1, wherein said thin semiconductor layer and said thin insulating layer are perforated with holes wherein nutrients are allowed to reach the retinal cells covered by said apparatus.

13. The apparatus of claim 1, wherein said thin insulating layer containing said stimulating electrodes is connected to said thin semiconductor layer containing CMOS circuitry by means of an extension of said thin insulating layer and conductive traces contained therein, thereby allowing said power and data for said circuitry to be received at a location remote from the region to be stimulated.

14. The apparatus of claim 13, wherein said remote location is the lens of the eye.

15. The apparatus of claim 13, wherein said remote location is in the anterior portion of the eye and in contact with the retina surface.

16. The apparatus of claim 1, wherein said electromagnetic radiation has a wavelength between 1 m and 1 km and said means to receive and transmit power and data comprise inductive coils.

17. The apparatus of claim 1, wherein the force exerted by the apparatus on the retina is not greater than 10 mm Hg.

* * * * *